United States Patent
Lorenz et al.

(10) Patent No.: US 8,685,022 B2
(45) Date of Patent: Apr. 1, 2014

(54) DEVICE FOR EXTERNALLY FIXING BONE FRACTURES

(75) Inventors: Kai-Uwe Lorenz, Speicher (CH); Heiko Durst, Speicher (CH)

(73) Assignees: Kai Uwe Lorenz (CH); Heiko Durst (CH); Marcel Hauser (CH); Jens Grasshoff (CH)

( * ) Notice: Subject to any disclaimer, the term of this patent is extended or adjusted under 35 U.S.C. 154(b) by 306 days.

(21) Appl. No.: 12/999,422

(22) PCT Filed: Jun. 17, 2009

(86) PCT No.: PCT/CH2009/000208
§ 371 (c)(1),
(2), (4) Date: Mar. 3, 2011

(87) PCT Pub. No.: WO2009/152633
PCT Pub. Date: Dec. 23, 2009

(65) Prior Publication Data
US 2011/0144643 A1      Jun. 16, 2011

(30) Foreign Application Priority Data

Jun. 17, 2008   (CH) .......................... 929/08

(51) Int. Cl.
*A61B 17/64*      (2006.01)
(52) U.S. Cl.
USPC ............................. 606/59; 606/256; 606/259
(58) Field of Classification Search
USPC ...................... 606/54–59, 246–279
See application file for complete search history.

(56) References Cited

U.S. PATENT DOCUMENTS

| | | | | |
|---|---|---|---|---|
| 3,858,578 A | * | 1/1975 | Milo | 600/229 |
| 5,449,206 A | * | 9/1995 | Lockwood | 285/261 |
| 5,649,925 A | * | 7/1997 | Barbera Alacreu | 606/86 A |
| 5,944,719 A | * | 8/1999 | Leban | 606/59 |

(Continued)

FOREIGN PATENT DOCUMENTS

| | | |
|---|---|---|
| DE | 10125742 C1 | 5/2001 |
| EP | 0807419 A | 11/1997 |

(Continued)

OTHER PUBLICATIONS

International Search Report dated Oct. 5, 2009, issued in corresponding international application No. PCT/CH2009/000208.

*Primary Examiner* — Jerry Cumberledge
(74) *Attorney, Agent, or Firm* — Ostrolenk Faber LLP

(57) ABSTRACT

A device (1) according to the invention for externally fixing broken bones (62, 62') of a patient, particularly the extremities, comprises a support (11) composed of a plurality of joint elements (2, 2) that are stringed together, wherein said support can be disposed outside the body of the patient. The proximal ends (41) of at least two percutaneously disposed pins (4) are anchored in the bone tissue (61) of the patient, and the distal ends (42) are fixed to the support (11). The joint elements (2) are stringed on a central tensile force element (3), and in each case two adjoining joint socket (22). The individual ball joints, and thus the support (11), can be fixed in a reversible frictionally engaged manner by applying a tensile force of the central tensile force element (3). The joint elements (2, 2') in turn are designed such that a pin (4) can be fastened to the support (11) in a clamping and/or frictionally engaged manner by applying the tensile force of the central tensile force element (3).

23 Claims, 8 Drawing Sheets

(56) References Cited

U.S. PATENT DOCUMENTS

| | | |
|---|---|---|
| 7,634,874 B2 * | 12/2009 | Lucas ............................ 52/108 |
| 7,785,325 B1 * | 8/2010 | Milbank ......................... 606/62 |
| 2003/0187432 A1 | 10/2003 | Johnson et al. |
| 2005/0131407 A1 * | 6/2005 | Sicvol et al. ................... 606/61 |
| 2005/0203509 A1 * | 9/2005 | Chinnaian et al. ............. 606/54 |
| 2007/0093813 A1 * | 4/2007 | Callahan et al. ............... 606/61 |
| 2007/0288011 A1 * | 12/2007 | Logan ............................ 606/61 |
| 2009/0018541 A1 | 1/2009 | Lavi |
| 2009/0048599 A1 * | 2/2009 | Hajianpour ................... 606/59 |

FOREIGN PATENT DOCUMENTS

| | | |
|---|---|---|
| JP | 2004/298253 A | 10/2004 |
| WO | WO 99/20194 A | 4/1999 |
| WO | WO 03/068085 A1 | 8/2003 |

* cited by examiner (a)        (b)

DEVICE FOR EXTERNALLY FIXING BONE FRACTURES

CROSS REFERENCE TO RELATED APPLICATIONS

The present application is a 35 U.S.C. §371 National Phase conversion of PCT/CH2009/000208, filed Jun. 17, 2009, which claims benefit of Swiss Application No. 929/08, filed Jun. 17, 2008, the disclosure of which is incorporated herein by reference. The PCT International Application was published in the German language.

BACKGROUND

1. Field of the Disclosure

The invention relates to a device for the external fixation of bone fractures, to joint elements for such a device, and to a method for the fixation of bone fractures, in accordance with the preambles of the independent claims.

2. Related Art

An external fixator is a device which is mounted outside the body and which is fixed to the bone via threaded metal rods called pins, for the purpose of external fixation of bone fractures of a patient, and is generally used on open fractures with soft-tissue damage or in cases of multiple injuries. In emergency operations on patients with multiple injuries, it is often necessary to defer the definitive treatment of bone fractures of the extremities, for example of the upper leg or lower leg, until other life-threatening injuries have been treated, so as not to put the life of the patient at risk. After a first reduction of the fracture, the latter is provisionally stabilized using an outer frame, the external fixator. In the case of open fractures, it may also be necessary to stabilize the fracture with an external fixator, since definitive primary treatment of the fracture by means of a plate, screw or nail would increase the danger of a post-operative infection. The subsequent removal of the external fixator and the definitive stabilization of the bone by means of a plate and screws or with nails take place, in the case of open fractures, after a clean wound has been obtained or, in the case of patients with multiple injuries, after a stable state has been achieved.

In what is called a pin fixator, pins, for example Schanz screws or Steinmann nails, are anchored in the bone tissue. Such pins are generally steel pins with standardized dimensions. After the bone fracture has been reduced, the pins are securely connected to one another using a rigid outer frame, which is often composed of interconnected bars or tubes. Alternative forms are the pinless fixator, the ring or halo fixator, and combined devices referred to as hybrid fixators.

When a patient who has suffered a high-degree open fracture (3° b or 3° c) is admitted to an accident and emergency unit, this fracture must not be stabilized directly with a plate or nail. Instead, an external fixator is initially fitted in these cases, and the method of treatment is then changed after a few days. The external fixator is dismantled and definitive osteosynthesis is performed, for example by plate or nail. The fitting of an external fixator is often very time-consuming in the known models, since many screws generally have to be tightened after the fracture has been reduced, and, if the position is unsatisfactory, they have to be undone again to allow correction and then tightened anew. If several corrections of position are needed, this procedure can take a very long time. Since patients admitted in emergency situations with high-degree open fractures are often seriously injured, for example with additional trauma to the chest or abdomen, the initial treatment of the bone fracture should be completed as quickly as possible in order to ensure that the patient can be moved as soon as possible to the intensive care unit. For the reasons set out above, this is not possible with the previous fixator systems. Some designs of external fixators also make anatomical adjustment of the bone fracture fragments difficult, since four or more bone pins have to be oriented on a straight line, which can be made difficult or impossible on account of the pin position. Moreover, the structure of the known fixator systems with bars and tubes is often large and bulky.

A number of fixator systems have been developed that are designed to permit better adaptation of the external fixator to the specific circumstances of a fracture.

DE 10125742 C1 discloses an external fixator in which a series of different individual modules provided with a through-opening are drawn onto a tensioning cable. The various types of individual modules have different lengths and/or contact angles. In addition, special connector elements for bone pins and retaining bars are provided. On a contact face at one side, the individual elements each have four studs, and, on the opposite side, they have four depressions, such that two successive individual modules can be arranged with a form fit and with four different rotation angles with respect to each other. After the fixator has been adjusted, the tensioning cable is tensioned. The individual modules are now also connected to each other with a force fit in the direction of the tensioning cable. Said external fixator permits only a relatively rough adaptation to the anatomical circumstances. Moreover, after the elements have been strung onto the tensioning cable, a fine adjustment to the position of the pins is no longer possible. Provision is also made that the bone screws are screwed into the bone only after the fixator has been set up.

U.S. Pat. No. 5,944,719 discloses an external fixator in which a chain of ball joints and sleeves are tensioned with a tensioning cable and stiffened. A plurality of sleeve elements have pivotable pin-holding devices, with which pins mounted in the bone tissue can be secured on the external fixator. For this purpose, the distal end of the pin has to be connected to the pin-holding devices via a nut. The distance of the fixator from the bone is therefore predefined by the length of the pins, which for this reason can only be short. By virtue of the ball joints, the fixator is movable and its shape can be adapted exactly to the anatomical situation. However, since the position of the holding devices on the fixator is predefined, or the fixator has to be correspondingly prepared when being assembled, said device is suitable in particular for planned operations, but less so for initial treatment under time constraints.

WO 99/20194 A1 discloses a similar device with a chain of ball joints that can be stiffened by means of a tensioning cable. In one embodiment, instead of the ball joint elements equipped with the pin-holding devices, sleeves are used that can be mounted subsequently on the fixator chain and that have pin-holding devices, such that the position of the holding devices can be adapted more quickly to the actual position of the pins.

WO 03/068085 A1 discloses a variant of a fixator with ball joint elements analogous to the abovementioned device, in which fixator the connections between the individual ball joints are fixed and released by means of a quick-clamping lever. This allows the fixator to be constructed in sequence from individual parts on site. However, in this embodiment, the overall shape cannot be adapted so quickly, because a large number of locks first have to be released.

SUMMARY

It is an object of the invention to make available a device that is of the kind mentioned at the outset and that does not have the abovementioned disadvantages or other disadvantages. In particular, such a device for the external fixation of bone fractures should permit simple reduction of a bone fracture by pins introduced into the bones, or the bone fragments, and a subsequent rapid and dimensionally stable stiffening of the device. A device according to the invention should preferably be able to be handled easily and with few maneuvers, even under stressful conditions. If the reduction is unsatisfactory, the device according to the invention should also be easy to unlock again in order to permit correction of the reduction and then renewed stiffening. A device according to the invention should also preferably be radioparent for the most part, in order to allow the reduction to be monitored. In addition, it should preferably also be able to be used in a nuclear magnetic resonance scanner.

A further object of the invention is to make available a method for the fixation of bone fractures that permits rapid and simple initial treatment of fractures but can also be used for definitive osteosynthesis.

These and other objects are achieved by a device according to the invention for the external fixation of bone fractures, by joint elements for such a device, and by a method for the fixation of bone fractures, in accordance with the preambles of the independent claims. Other preferred embodiments are set forth in the dependent claims.

A device according to the invention for the fixation of bone fractures is composed of a stiffenable support made up of individual joint elements which are arranged in series on a central flexible tensile force element. Two adjacent joint elements in each case form a ball joint. Conventional pins, which are anchored beforehand in the individual bone fragments to be fixed, are held clamped by the joint elements, and the bone fragments are in this way spatially stabilized in relation to each other. The secure clamping of the pins and the stiffening of the device take place simultaneously, by means of a sufficiently high tensile force being applied to the tensile force element. The contact faces of the ball joints are thus pressed against each other, resulting in a stable frictional connection between the individual joint elements of the device, and the device is fully stiffened. The pins are securely clamped at the same time, either between two adjacent joint elements or with two-part joint elements. Upon release of the tensile force, the device is unlocked again and the connection to the pins released.

In a preferred variant of a device according to the invention, the tensile force element is already pretensioned with a certain tensile force in the unlocked state, with the result that, when the device is fitted in place, it holds provisionally on the pins, and yet the fixator device can still easily be brought to the desired shape by the operator when the fracture is reduced. After being let go, the device according to the invention maintains the shape provisionally.

All suitable materials, in particular metals and fiber-reinforced plastics, can be used both for the tensile force element and also for the joint elements. However, for the tensile force elements, it is preferable to use wires, cords, cables or particularly preferably fiber bundles (also referred to below simply as bundles) made of metal, carbon fiber, or of other suitable plastics or combinations of the aforementioned materials which, with a low weight, are able to take up very high tensile forces, without deforming even over a period of months. For the ball joint elements, fiber-reinforced polymer materials are preferably used in order to ensure a high degree of mechanical stability with at the same time a low weight. Such a choice of the materials also has the advantage that the device according to the invention is radioparent and also has no metal parts that would cause artefacts in a nuclear magnetic resonance scanner or would prohibit its use in the magnetic field of the nuclear magnetic resonance scanner.

In a method according to the invention for the fixation of bone fractures, conventional pins are anchored in the patient's bone tissue. Normally, two pins are used for each large bone fragment, that is to say a total of at least four pins. For mechanical reasons, the distance between the pins on the same fragment is chosen to be as great as possible. The pins are then latched onto a fixator device according to the invention. The individual elements of the device are pivotable relative to one another in the unlocked state and follow the movements of the pins in the resetting of the bone by the operator. By the tensioning of a central tensile force element, the joint elements are blocked relative to one another and also remain in the previously adjusted position under a load. In this way, the fractured bone is held fixed in the adjusted position, which is as far as possible the original anatomical position. At the same time, the pins are securely clamped and stable in the desired position on the device.

In principle, the fixator device according to the invention is provided for temporary treatment prior to the definitive treatment of a fracture with nails or plates, but, because of its advantages in terms of handling and weight, it is intended especially for use in emergency situations. Another field of application is destined to be in disaster situations, for example earthquakes, or war situations, where seriously injured patients have to be made ready for transportation in the shortest possible time by emergency means. However, a fixator device according to the invention is also just as suitable for the definitive treatment of a fracture.

BRIEF DESCRIPTION OF THE DRAWINGS

The device according to the invention is explained below with reference to the drawings.

DETAILED DESCRIPTION OF THE EMBODIMENTS

Figure 1:
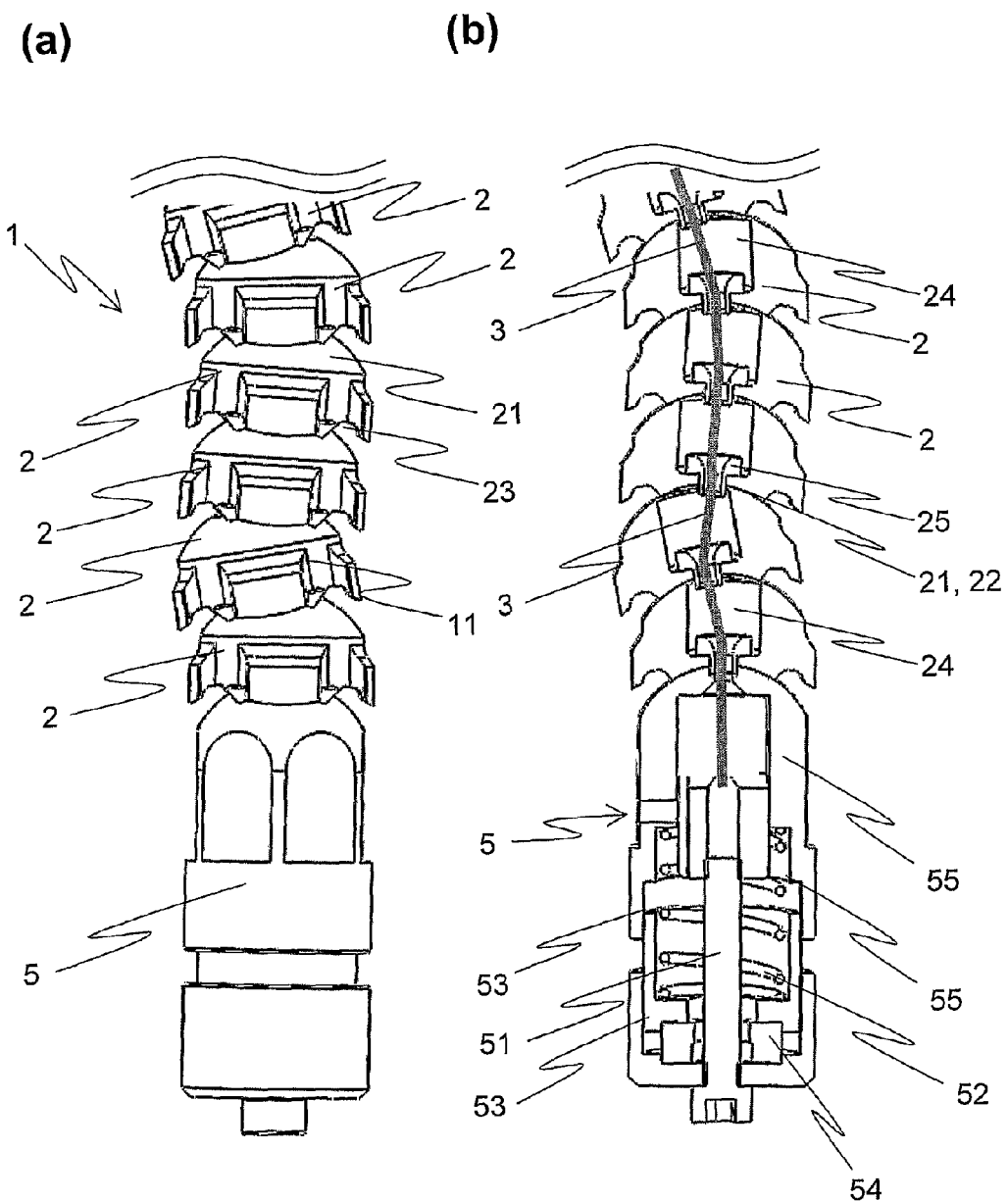
FIG. 1 shows an example of the rear end of a device according to the invention, (a) in side view, and (b) in a longitudinal section.

A possible embodiment of a device 1 according to the invention for the external fixation of bone fractures is shown in FIG. 1, (a) in side view, and (b) in a longitudinal section.

The rear end of the support 11 of the device 1 is shown, comprising the six rearmost joint elements 2 and, at the end, a tensioning device 5 for generating the tensile force needed for stiffening the device 1. The tensile force element 3 running along the entire length of the support 11 extends from the tensioning element 5 through the longitudinal passages 24 of the joint elements 2 and finishes, at a front end (not shown) of the support, in an abutment which takes up an applied tensile force and transmits this to the joint elements 2. The tensile force element is preferably designed as a fiber bundle which, with the least possible thickness, has the greatest possible tensile strength. Suitable bundles for this purpose are, for example, wire bundles, carbon fiber bundles, or bundles made of other suitable plastics. The latter have the additional advantage of being radioparent and of not being sensitive to magnetic fields.

The individual joint elements 2 have an upper ball joint surface in the form of a spherical cap 21, and a lower ball-joint surface in the form of a joint socket 22, wherein the spherical cap 21 of one joint element 2 lies in each case in the joint socket 22 of the next joint element 2, thus resulting in a sequence of ball joints. During the fitting of the fixator device 1, the tensile force element 3 is not subject to a tensile force or is subject to only a low tensile force, such that the frictional engagement between the ball joint surfaces 21, 22 of two adjacent joint elements 22 is low, and the individual ball joints can be oriented and arranged as desired by the operator. When the tensile force is increased, the static friction between the ball-joint surfaces 21, 22 becomes so high that a strong frictional connection is obtained between the individual joint elements 2, and the device 1 is stiffened in such a way that it can no longer be deformed without being destroyed.

The joint elements can be made of metal or of a suitable high-strength plastic. Since they are exposed to quite high compressive forces at the contact surfaces 21, 22 over a long period of time, the material should have a high creep resistance. Fiber-reinforced plastics, for example, are especially suitable. The surfaces intended to engage on each other with static friction can be suitably treated in order to increase the coefficient of friction. For example, they can be roughened or coated. The contact faces can also be provided with a toothing.

It is possible for the orientation of the ball-joint elements to be chosen the other way round, such that the spherical caps are directed toward the tensioning device. A configuration is likewise possible in which two different types of joint elements are alternating stringed together with each other, of which a first type has two spherical caps, and a second type has two joint surfaces.

The tensioning device 5 is used to tension the tensile force element 3. A tensioning device 5 can be configured in different ways, preferably with only a low force needing to be applied in order to achieve the relatively high tensile force during stiffening, and without any substantial lever forces having to be applied, which could be transmitted to the fracture. In the example shown, a threaded bolt 51 is turned by means of a suitable rotary tool, e.g. hexagon key, cordless screwdriver, crank handle, torque wrench, as a result of which a compression spring 52 arranged in a housing 53 is compressed via a plate 54 with an opposite thread. In order to take up the shearing force of the rotary tool, the tensioning device 5 has to be fixed, for example by hand or with tongs, particularly so the abutment 55 directly in contact with the first joint element 2. The counteracting spring force of the spring element 52 leads to a force being applied to the bolt 51. The bolt 51 is connected to the tensile force element 3 by a freely rotating coupling and thus transmits the spring force to the tensile force element and therefore to the joint elements 2. However, the individual joint elements 2 do not move here, such that the position of the pins in the final stabilization is not changed. As is described in greater detail below, the spring 52 applies a force that tensions the joint elements against one another. Upon further tightening of the threaded bolt 51, the spring element is completely compressed and the housing 53 comes to lie with an end face 53 on an opposite step 55 of the abutment 55. The spring travel is now equal to zero and, upon further tensioning of the element 3 taking up the tensile force, the respectively adjacent joint elements are accordingly pressed increasingly more tightly against each other.

In the example shown, the tensioning device 5 is an integral component part of the device 1 according to the invention. Alternatively, however, it is also possible for the tensioning device 5 to be designed in two parts, with an abutment which is arranged on the rear end of the device and which serves to maintain the tensile force, and with an actuator device which serves to generate the tensile force and, for this purpose, is mounted temporarily on the device according to the invention. Many devices for generating a tensile force are known from machine engineering. However, permanently mounted, one-part clamping devices should have a space-saving and light-weight design, so as not to cause problems on account of their volume or weight. This limits the technical design possibilities but allows the device to be fitted without complicated aids. By contrast, in two-part designs of the tensioning device 5, it is possible to generate higher tensile forces without a human operator having to exert considerable strength when generating these tensile forces, or without the device according to the invention being exposed to substantial shearing forces during operation.

Alternatively, a spring element, for example, can be tensioned using a suitable pneumatic, hydraulic or electric actuator device and can then be locked with the tensile force element, for example with a locking nut, such that the actuator device can then be removed again. In the simplest case, for example, an actuator device can also be a pneumatically or electrically operated rotary key.

In another possible embodiment, a spring force element can also be mounted on an abutment arranged at the front end of the device. Instead of separate spring elements, the elastic extension of a steel bolt or of the tensile force element itself can also be used as spring force element. For example, a threaded bolt connected to the tensile force element can be hydraulically pretensioned with a defined tensile force, after which the bolt is fixed with a locking nut without force being applied, and the hydraulic tensile force is then removed again. It is also possible to use a tensioning device in which, after the device has been fitted, a trigger is actuated which has the effect that the tensile force element and the spring element are instantaneously subjected to the tensile force, and the device according to the invention is therefore stiffened immediately.

Figure 2:
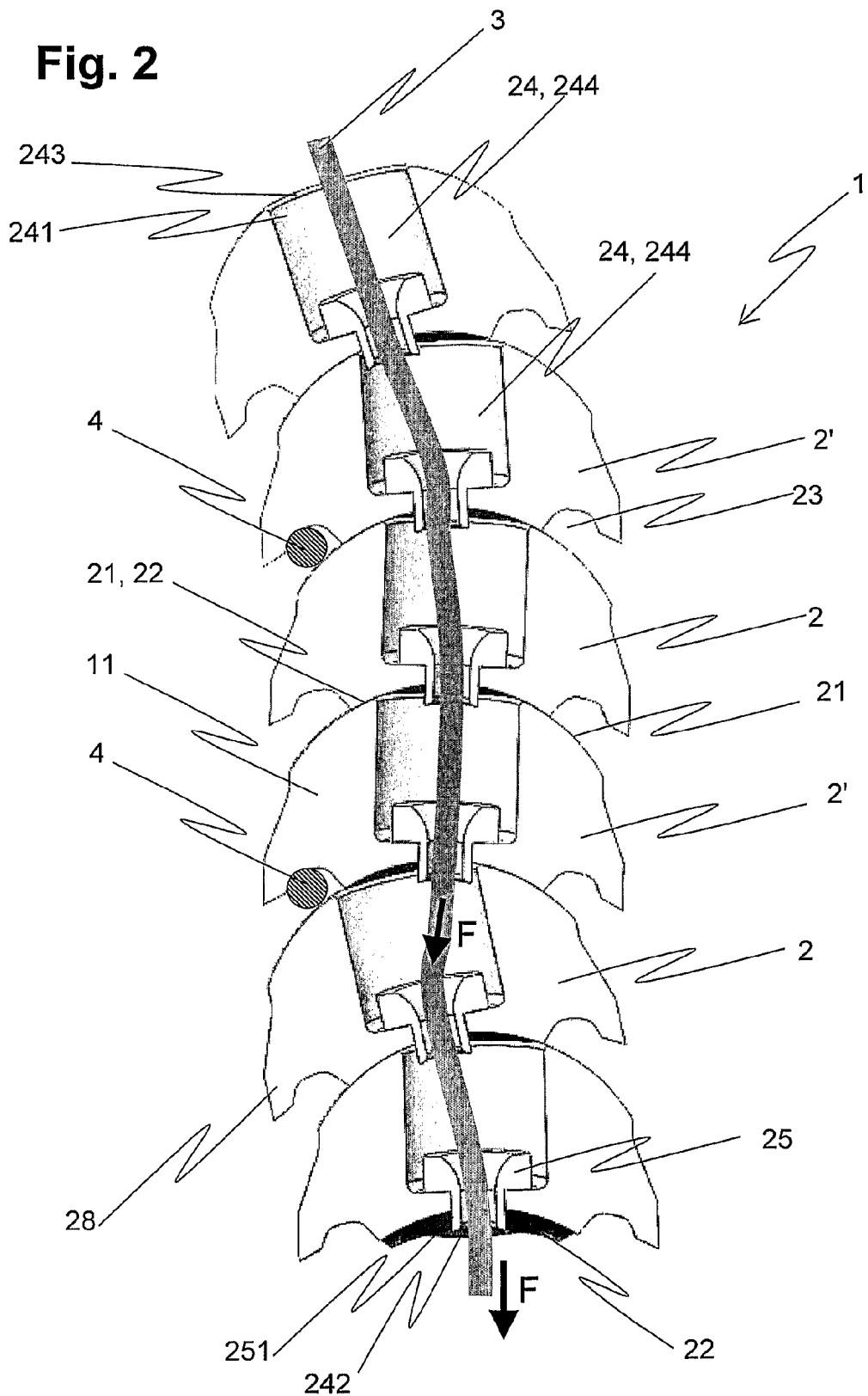
FIG. 2 shows a longitudinal section through a part of a device according to the invention analogous to FIG. 1, with another embodiment of the joint elements.

FIG. 2 shows, likewise in a longitudinal section, a part of a fixator device 1 according to the invention analogous to FIG. 1, with two pins 4 shown in cross section, which are each held clamped between two joint elements. The two pins 4 anchored in the bone tissue are connected to the support 11 of the device 1 with a form fit and a force fit, by means of being fixed by clamping between the spherical cap 21 of a first joint element 2 and a receiving groove 23 of an adjacent joint element 2'. To mount the pins 4 on the device 1 according to the invention, they are latched into the gap between receiving groove 23 and spherical cap 21, with the second joint element 2' being temporarily lifted slightly from the first joint element 2. It is also possible for this provisional securing to be effected via a kind of snap-fit mechanism that holds the pin provisionally in place.

According to another embodiment not shown in the figures, the position of the receiving groove in relation to the two joint elements is the other way round from what has been described above. In this case, the receiving groove is arranged on a spherical cap of a first joint element, and the adjacent, second joint element has a joint socket without receiving groove. Spherical cap and joint socket again together form a ball joint and, when a tensile force is applied to the central tensile force element, a pin can be fixed with a form fit and force fit between receiving groove and joint socket.

On the basis of the present disclosure, it is obvious to a person skilled in the art that the geometry of the receiving groove is adapted to the outer contour of the pins. If an additional means of securing the pins against rotation in the fixed position is to be achieved, the cooperating surfaces can either be suitably roughened and structured or, for example, can be polygonal in cross section.

The joint elements 2 all have a longitudinal passage 24 which, independently of the shape of the support 11 of the device 1, forms a continuous channel extending from the tensioning device at the rear end to the abutment at the front end of the device, in which channel the tensile force element 3 runs. In the example shown, the longitudinal passage 24 is composed of a cylindrical cavity 244 which is open 241 toward the spherical cap 21 and in the bottom of which a smaller lower opening 242 leads to the joint socket 22. In principle, it is preferable that the tensile element is routed through the center of the radius of the spherical cap.

The longitudinal passage can of course also be conical, although a cylindrical design is advantageous in production methods involving removal of material. As regards the design of the longitudinal passage, it should be ensured in principle that the contact face between the spherical cap and the joint socket of the ball joint is sufficient in all orientations of the ball joint, and toward all sides, to ensure a stable support of the joint under tension and to avoid buckling of the support.

Figure 3:
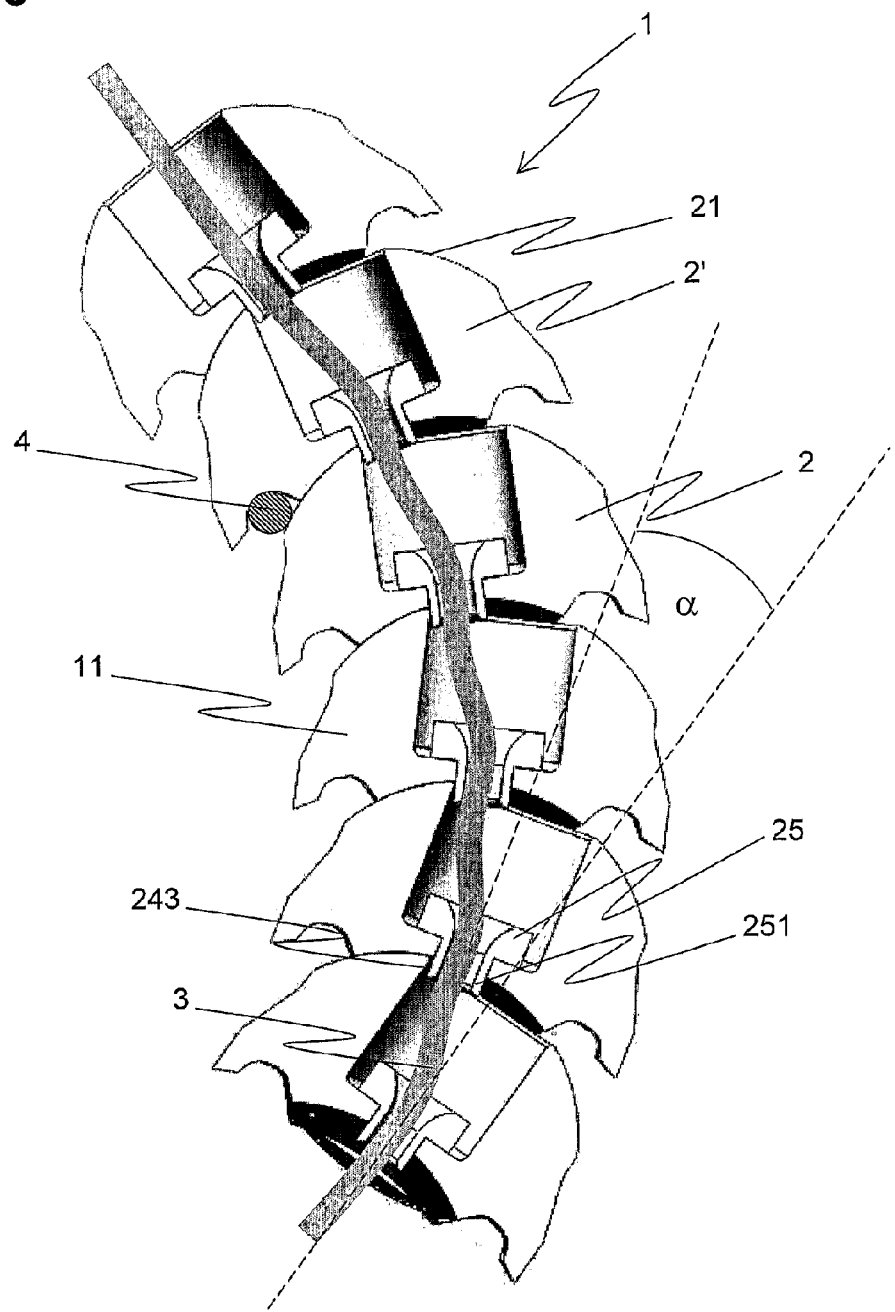
FIG. 3 shows a longitudinal section through a part of a device according to the invention analogous to FIG. 2, at the maximum bending angle.

FIG. 3 shows, in longitudinal section, a part of the support 11 of the same device 1 as in FIG. 2, at the maximum bending of the device. In principle, the maximum pivot angle a of two joint elements 2, 2' relative to each other is determined by the edge 243 of the upper opening 241 of the longitudinal passage 24, on which edge 243 the tensile force element 3 abuts at the maximum pivoting. In the example shown, the pivot angle can be up to 15°. However, the abutting action of the tensile force element 3 can have the effect that shearing forces act on the tensile force element 3 at the edge 243 and can lead to signs of wear. Moreover, despite having extremely high tensile strength, the carbon fiber materials particularly advantageous for the tensile force element 3 are very sensitive to such shearing forces. In the illustrative embodiment of the joint element 2 shown here, a deflection element 25 is therefore arranged on the lower opening 242 of the longitudinal passage 24, which deflection element 25 protects the tensile force element 3 from the edge of the lower opening 242 and limits the minimum bending radius of the central tensile force element 3 at the bottom. The deflection element 25 has a stud 251 which extends through the lower opening 242 and protrudes beyond the joint socket 22. The stud 251 thus forms an abutment that limits the maximum pivoting of the joint elements 2, 2' relative to each other, and said stud 251 also protects the tensile force element from the edge 243 of the upper opening 241 of the adjacent joint element 2.

In order also to protect the tensile force element 3 from potentially damaging shearing forces caused by the rotation of the joint elements 2, 2' relative to each other, the deflection element 25 should have the lowest possible coefficient of friction, such that the tensile force element 3 and the joint elements 2, 2' are substantially mechanically uncoupled in terms of rotation. The material of the deflection element is chosen such that the tensile element does not cut into said deflection element, and such that the deflection element does not deform when the tensile element bears on it and is tensioned. The joint element 2 and the deflection element 25 can also be formed in one piece, which can be cost-efficient particularly in production by injection molding.

Figure 4:
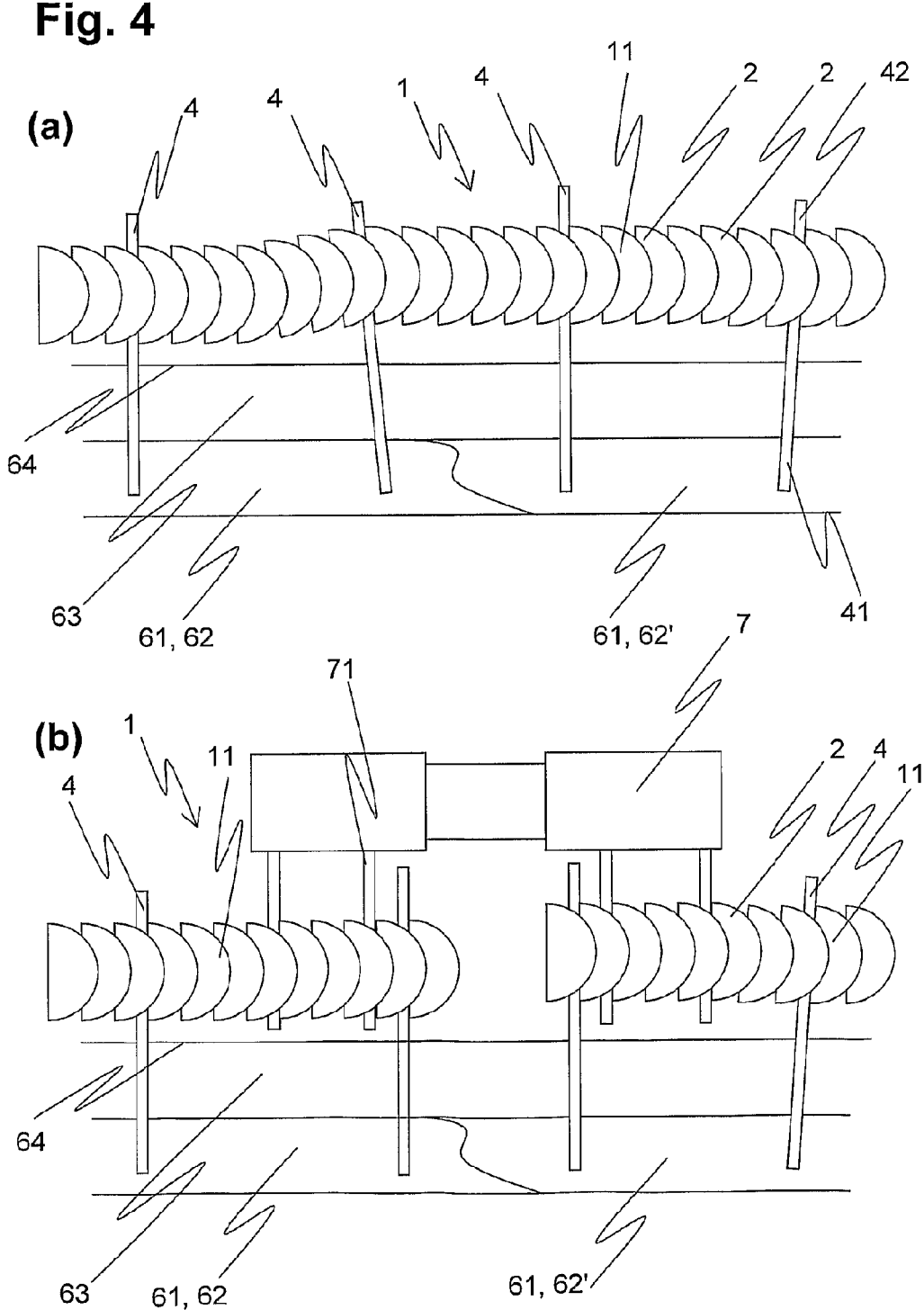
FIG. 4 shows schematically (a) a bone fracture stabilized with a device according to the invention, and (b) an embodiment with two supports and with an intermediate element arranged between them.

The use of a device according to the invention is shown in a highly schematic form in FIG. 4. The position of the pins in and relative to the individual bone fragments is indicated only roughly in the drawing and, when in actual use, the pins are positioned not only through one cortical layer but through two cortical layers. After the fracture has been reduced, a plurality of pins 4 are anchored by known methods in the bone tissue 61 of the individual bone fragments 62, 62' of a patient. Four to six pins are generally fitted. For use with the device 1 according to the invention, the pins 4 can be positioned without great consideration being paid to the external fixator that is still to be applied. In the reduction of open fractures in an emergency situation, where a definitive osteosynthesis by plate or nail subsequently takes place, correction is not generally made exactly to the nearest millimeter; here the fragments are sometimes still dislocated by up to 5 to 10 mm. In light of the accompanying injuries, it is rapid treatment that is important, not the perfect reduction of the fracture. It is primarily important that no fragments press against the skin, nerves, muscles or blood vessels. By contrast, in reduction by definitive osteosynthesis, it is sought to achieve less than 5 mm dislocation and 5° axial deviation.

After the pins 4 have been fitted, and after a first provisional reduction of the fragments, the pins 4 are simply latched onto the fixator device according to the invention. The pivotability of ca. 15° between adjacent joint elements and the free rotatability of the latter mean that pins 4 lying obliquely with respect to each other can also be fixed without problem. The distances between the pins can also be chosen largely without measuring. The flexibly shapeable support 11 of the device according to the invention can easily reproduce these irregularities.

In a preferred version of the device according to the invention, a first and relatively low tensile force of between 100 and 200 N is already applied to the tensile force element in the fitted state, such that frictional engagement is already present between the individual joint elements 2. This pretensioning is chosen such that the frictional engagement can be easily overcome during manual alignment, and there is enough play to ensure that that the pins can be latched into the receiving grooves 23 of the joint elements 2, and the force fit and frictional engagement between pins and joint elements prevent spontaneous slipping of the pins. Another advantageous effect of this low pretensioning is that the chain-like support is not so shaky and does not sag during the reduction. The chosen pretensioning is only so great that the joint elements can still be easily moved relative to each other in order to reduce the fracture. The low pretensioning is accordingly too low to keep the fracture reduced.

In order to generate the pretensioning, it is possible, as is shown in FIG. 1b for example, to use a spring element 52, which not only provides the force for the pretensioning but also the spring travel for the latching-in of the pins. In the pretensioned state, the device according to the invention can also still be moved by hand after the pins 4 have been latched in, such that the fracture can be correctly aligned. This can be monitored by means of radioscopy. If the position of the bone fragments is satisfactory, the tensioning device (not shown in FIG. 4) is actuated, as a result of which the joint elements 2 are drawn against each other by the tensile force element and are blocked by means of static friction. The fixator device according to the invention is now stiffened. The position of the pins 4 is not changed by this stiffening procedure. In order to keep the fracture reduced, a greater tensile force of 500 to 2000 N has to be applied. This is preferably possible by manual operation. The device is now provisionally secured. Thereafter, the tensile force is increased to a final value of 5000 to 15000 N, preferably with an actuator device.

In other embodiments not shown in the figures, a two-stage motorized torque wrench is used with which a first, lighter stage of pretensioning can be built up. A second tensioning stage with greater pretensioning is built up only when the spring is completely compressed. For the definitive fixing of the fixator, the second, high stage of the two-stage torque wrench is switched on. The counter-hold must in this case be provided using a tool, for example tongs or a fork wrench. Alternatively, this definitive fixing can be effected using a manual torque wrench.

The device according to the invention is preferably designed in such a way that the tension does not subside over several months, or subsides only to an inappreciable extent. It is also possible for a device according to the invention to be equipped with an optical indicator which, for example, shows different colors, numbers and/or letters depending on tensile force and/or mode (fitting mode, tensioning mode, first and second stage, etc.). Pressure sensors of various types can also be used to determine and monitor the actual tensile force applied.

It may be necessary to fit other pins subsequently. In such a case, the already stiffened device has to be unblocked in order to latch the new pins onto the support. For subsequent fitting, however, adapter elements are preferably used which can be mounted reversibly with a form fit and/or force fit on the stiffened device according to the invention and which have a suitable holding device for the additional pin. For example, WO 2007/001945 A1 discloses a clamping device suitable for this purpose. Such adapter elements can also be used for mechanical coupling to other fixator devices.

Figure 5:
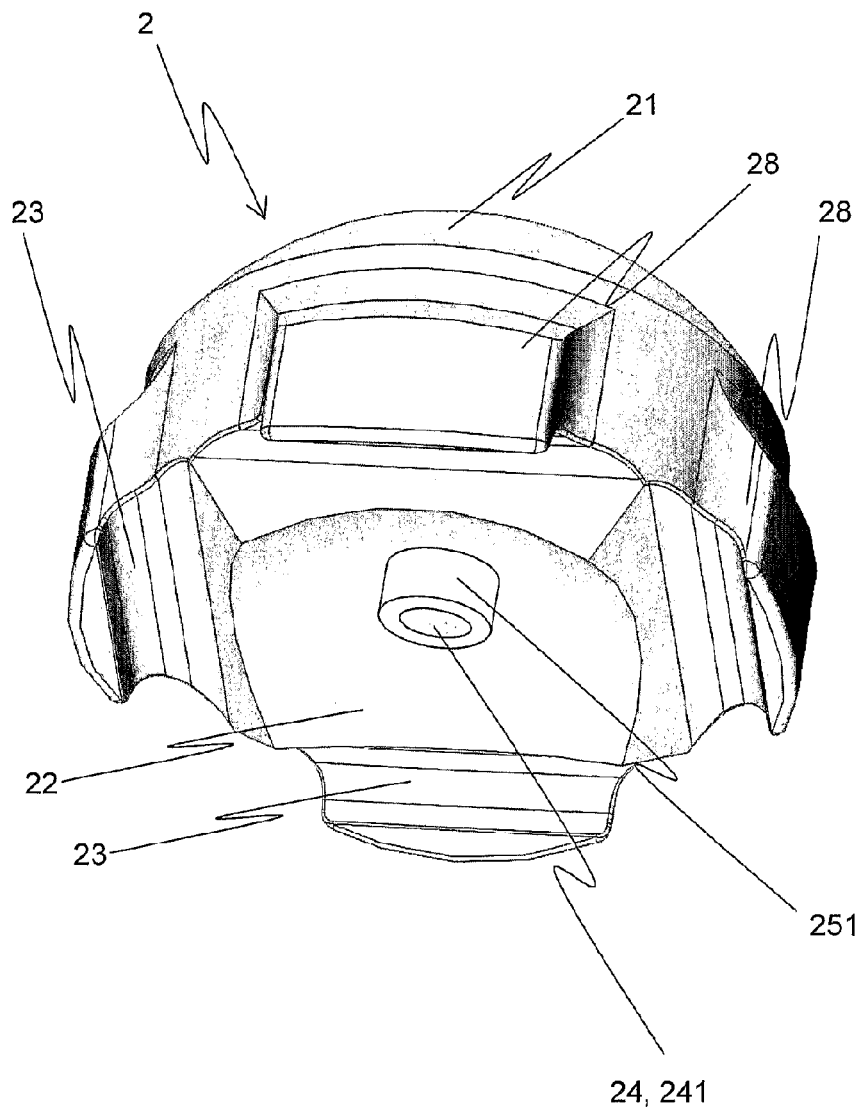
FIG. 5 shows a possible embodiment of an individual joint element of a device according to the invention, analogous to FIG. 1.

An individual joint element 2 of the device according to the invention from FIG. 1 is shown in FIG. 5, in a view directed obliquely to the joint socket 22. The joint element 2 has substantially the outer shape of a short cylinder, with a spherical cap 21 on an upper end, and with a joint socket 22 on the opposite lower end, from which joint socket 22 the stud 251 of the deflection element 25 protrudes. Four teeth 28 are formed integrally on the peripheral surface of the cylinder, with a groove 23 for receiving a pin being present in each case between a tooth 28 and the joint socket 22. At a tensile stress of 5000 N, a clamping torque of 1 to 5 Nm can be achieved for this pin holder. In principle, the distance between receiving groove 23 and tensile force element 3 should be as short as possible, in order to achieve the best possible clamping effect. The surface of the receiving groove 23 can be suitably configured in order to achieve the highest possible coefficient of friction, for example by means of a suitable profile or by means of a coating that increases friction.

Figure 6:
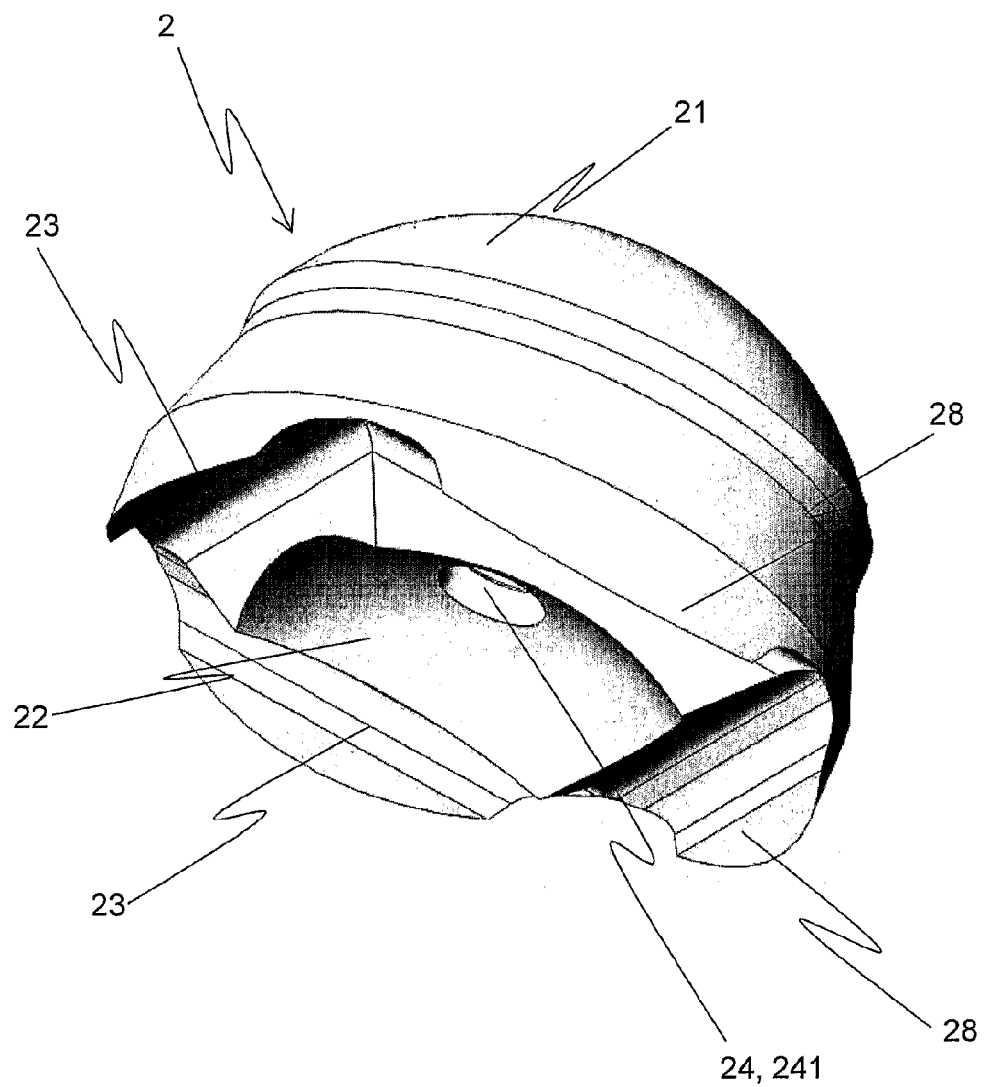
FIG. 6 shows another possible embodiment of an individual joint element of a device according to the invention, analogous to FIGS. 2 and 3.

FIG. 6 shows another possible embodiment of an individual joint element 2 of a device according to the invention, as is shown in FIGS. 2 and 3. The deflection element with stud has been omitted in order to make the through-opening 24, 241 visible. This variant is particularly suitable for a method of production that involves removal of material. After a rotationally symmetrical main body has been turned and the longitudinal passage 24 has been drilled, the four receiving grooves 23 are milled out.

The diameter of a joint element of a device according to the invention is typically between 30 and 40 mm, with a compromise having to be made between mechanical stability and the space taken up. For example, in the variant of the device according to the invention from FIG. 1, the diameter of the joint elements 2 is preferably 40 mm, the height 23 mm, and the sphere radius of the spherical cap 20 mm. In the stretched state, this results in a distance of 20 mm between two individual joint elements. The shape and position of the receiving grooves 23 is adapted to the diameter of the pins that are to be clamped, which diameter is a standard 5 mm, although the customary pins can also have a diameter of 4 mm or 6 mm. Joint elements with different grooves for different pin diameters are also conceivable. In principle, only one receiving groove would be necessary, since the joint elements of a device according to the invention are freely rotatable about their longitudinal axis.

In another possible embodiment of a device according to the invention, a groove can also be formed on the spherical cap 21, such that a pin lies both in the receiving groove 23 and also in the groove on the spherical cap 21. Alternatively, the groove can also be designed as an annular groove extending around the spherical cap 21. This variant affords the advantage of a greater contact surface between pin and spherical cap, but it also means that the two joint elements involved have to be flush along their longitudinal axis and oriented with the correct rotation angle, which reduces the flexibility of the support at this point.

Figure 7:
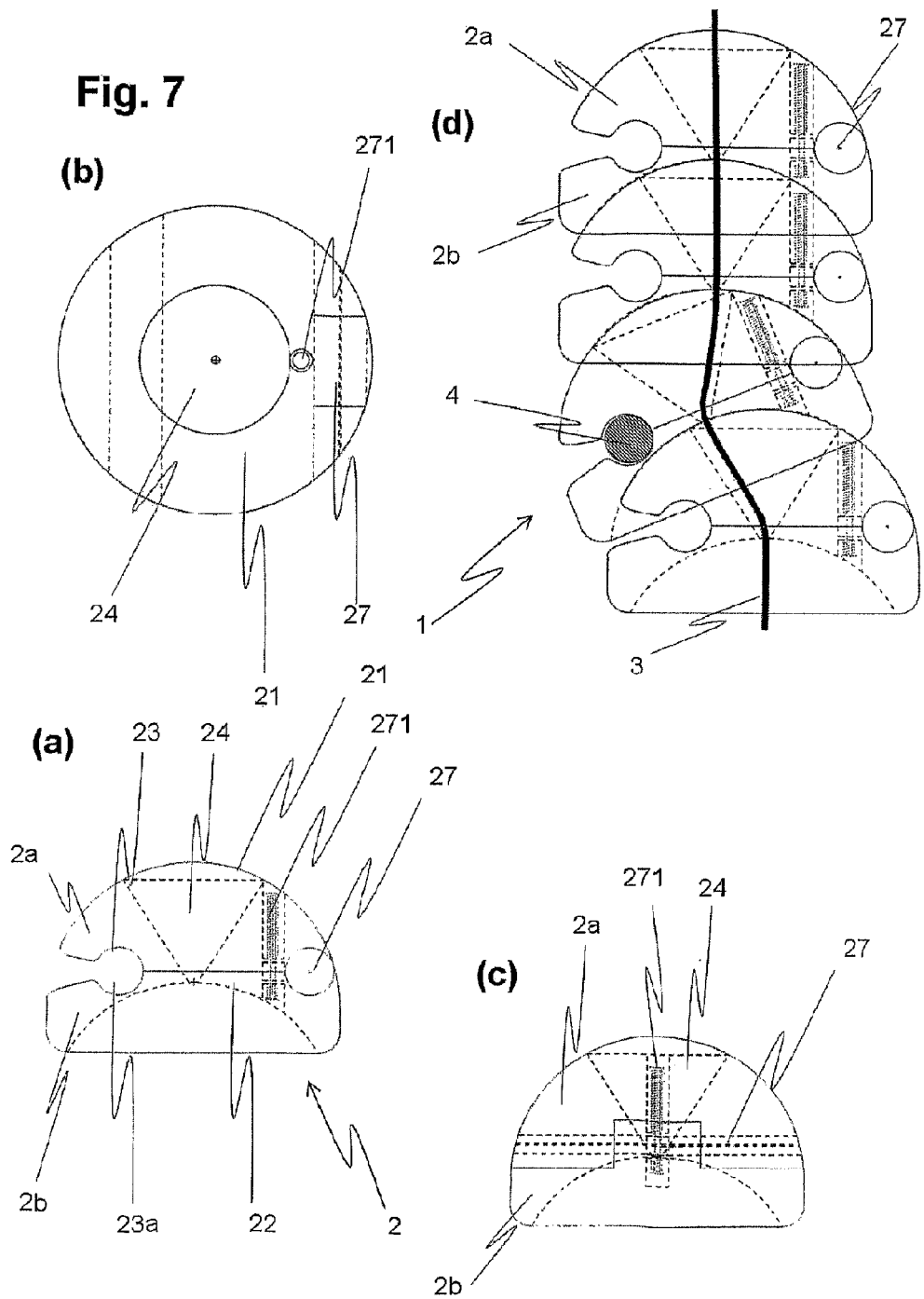
FIG. 7 shows a two-part embodiment of a joint element for a device according to the invention.

Instead of being designed as a one-part body, the joint elements can also be designed in two parts. Thus, FIG. 7 shows, for example, a two-part embodiment of a joint element 2 with an upper part 2a, which has a spherical cap 21, and with a lower part 2b which is pivotably connected to the upper part 2a via a hinge 27 and which has a joint socket 22, (a) in a side view looking toward the hinge axis, (b) in a plan view looking along the longitudinal axis, (c) in a side view perpendicular to the hinge axis, and (d) in a part of a support 11 corresponding to the device 1 according to the invention. Arranged on the mutually facing inner sides of the two parts 2a, 2b there are two parallel receiving grooves 23, 23a, between which a pin can be securely clamped. Since the tensile force of the tensile force element 3 extends substantially perpendicular to the axis of the hinge 27, the joint 27 can be relatively light. Said embodiment is especially robust and allows the receiving grooves 23, 23a to be placed closer to the tensile force element 3, thus resulting in a higher clamping torque.

Figure 8:
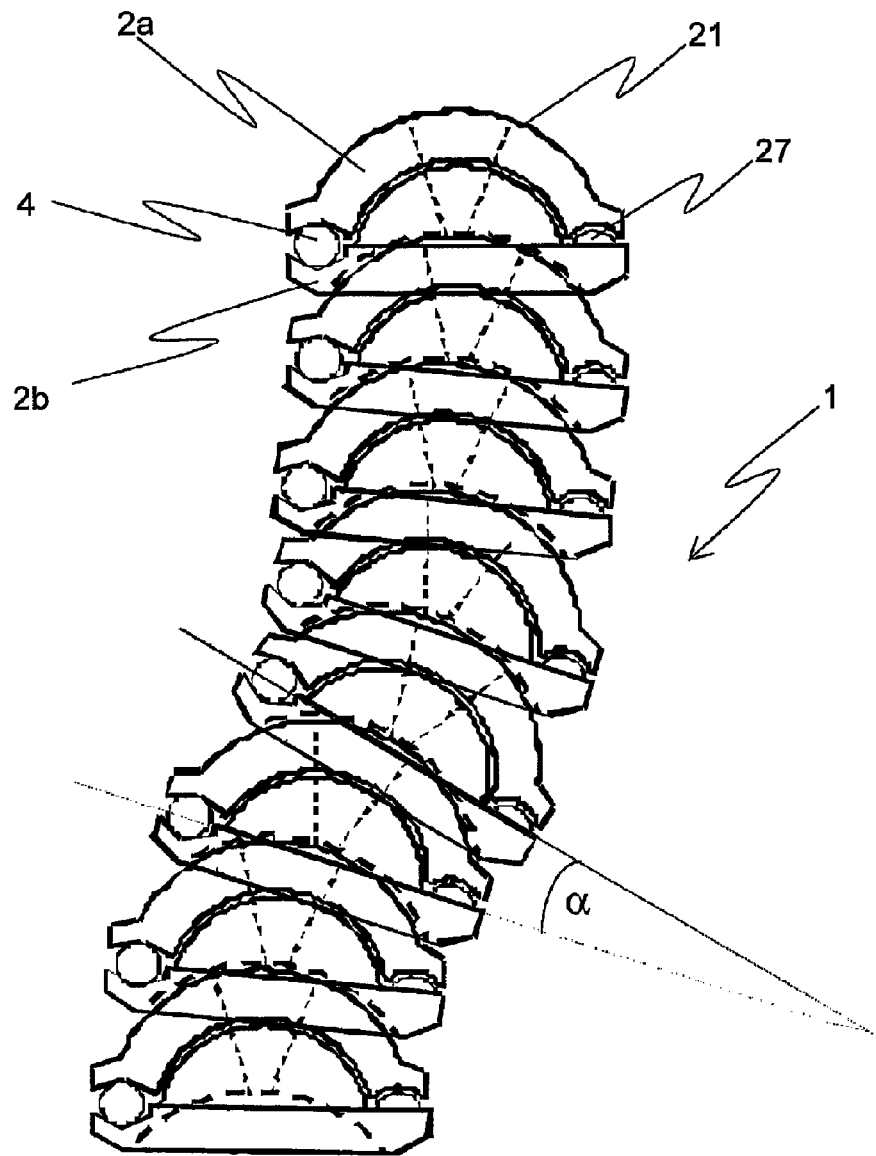
FIG. 8 shows another variant of a device according to the invention with a two-part joint element.

As was also the case in the one-part embodiments of the joint elements discussed above, the clamping force for fixing the pin is also generated by the central tensile force element 3 in the two-part variant. The example from FIG. 7 also has a further spring element 271, for example in the form of a tension spring, which additionally applies a slight spring force to the two parts 2a, 2b, such that the pins can be provisionally secured when the device 1 according to the invention is fitted. These integrated spring elements 271 can also be omitted, in which case a spring force for the provisional securing is effected analogously to the one-part embodiment. Another variant of a device 1 according to the invention with joint elements 2 in two parts 2a, 2b and without a spring element is shown in FIG. 8.

In another preferred embodiment, a device according to the invention has coupling means for coupling the device to other fixator devices or to additional devices. For example, a screw coupling can be mounted on a front end of the device according to the invention and allows the latter to be connected to a front end of another device according to the invention or to a coupling element. A coupling element is also conceivable, for example, in the form of a plate with several suitably arranged pins which can be latched into two devices that are to be connected and in this way connect them. Intermediate segments can also be introduced in this way, for example to bridge larger distances. Longer external fixators, for example from the hip to the ankle, are preferably composed of two or more individual devices according to the invention, since the necessary tensile forces increase in proportion to the length of the fixator device. If necessary, other components can be integrated into the fixator device according to the invention, for example components which permit distraction, correction of the axis or lengthening, and via which it is thus possible to influence the healing of the fracture. Examples are distraction elements and shock-absorbing spring elements. It is also possible for individual joint elements or for all of the joint elements to be designed in such a way that they can be lengthened.

A device according to the invention can also be connected in a star shape to two or more additional devices according to the invention via a suitable coupling element. In this way, for example, a hybrid fixator can be produced comprising a device according to the invention which is secured on pins and which merges on a coupling element into two to four arms, which are likewise designed as a device according to the invention and are connected to a ring fixator.

In a method according to the invention, groups of pins on two sides of a fracture can also be connected in each case with a device according to the invention or a support 11. An intermediate element 7 is then fitted between them and, for example, permits a subsequent distraction or correction of the axis, for example during a follow-up correction on the ward or at a consultation. Such an embodiment with an intermediate element is shown schematically in FIG. 4(*b*). The intermediate element 7 is connected by four pins 71 to the two supports 11 of the devices 1. Damper elements that permit adjustment of the hardness of the overall construction can also be integrated in such an intermediate element 7. Such elastic fixing of fractures may be desirable, for example, in order to achieve better healing in certain cases.

According to other embodiments of the invention that are not shown in the figures, two or more short support elements or partial elements are connected to give a support having a desired length. The individual partial elements are latched together in order, on the one hand, to achieve the definitive length of the required support and, on the other hand, to make available the required type of fixator. Thus, a fixator in the sense of a single coil (for the multiply injured trauma patient during the night) or a fixator with a coil element at both ends and a damper element or a correction element in the middle (for the definitive treatment of a fracture) can be assembled. The elements are connected by couplings, these couplings permit, on the one hand, the connection of the elements and, on the other hand, the transmission of the central tension (from tensile element of element 1 to the tensile element of element 2 to the tensile element of element 3). In other words, despite several elements being coupled, only one tensioning device is still needed at one side.

According to other advantageous embodiments, tensioning devices can also be arranged at both sides of the devices according to the invention.

LIST OF REFERENCE SIGNS 1 external fixator, device for external fixation support
11 2, 2' joint element
2a, 2b part of a joint element
21 spherical cap
22, 22' joint socket
23, 23a groove for receiving the pin
24 longitudinal passage
241 upper opening
242 lower opening
243 edge
244 cavity
25 deflection element
251 stud
27 hinge
271 spring element
28 tooth
3 central tensile force element
4 pin
41 proximal end
42 distal end
5 clamping device
51 bolt
52 spring element
53 housing
54 plate
55 abutment
61 bone tissue
62, 62' bone fragment
63 soft tissue part
64 skin
7 intermediate element
71 pin

What is claimed is:

1. A device for the external fixation of bone fragments of a patient, particularly of the extremities, with a support, which can be arranged outside the body of the patient comprises:
   a plurality of directly stringed together joint elements forming the support; and
   at least two percutaneously arranged pins which are adapted to be anchored with their proximal end in the bone tissue of the patient, securable by their distal end and fixable in their spatial position relative to each other;
   which joint elements are stringed together on a central tensile force element, and two adjacent joint elements in each case together form a ball joint with a spherical cap and a joint socket, and the individual ball joints, and therefore the support, are reversibly fixable with a force fit, by frictional engagement, by applying a tensile force to the central tensile force element; and
   which joint elements are configured such that by applying the tensile force to the central tensile force element at least one percutaneously arranged pin is clamped directly between the joint elements while at the same time the individual ball joints, and therefore the support, are being reversibly fixed.

2. The device as claimed in claim 1, wherein a first joint element of the support has a spherical cap, and an adjacent, second joint element has a joint socket and a receiving groove, said spherical cap and joint socket together forming a ball joint, in which case the at least one percutaneously arranged pin is clamped directly between the receiving groove and the spherical cap by applying a tensile force to the central tensile force element, or in that a first joint element of the support has a spherical cap and a receiving groove, and an adjacent, second joint element has a joint socket, said spherical cap and joint socket together forming a ball joint, in which case the at least one percutaneously arranged pin is clamped directly with a form fit and force fit between receiving groove and joint socket by applying a tensile force to the central tensile force element.

3. The device as claimed in claim 1, comprising a joint element including two pivotably connected parts, of which a first part has a spherical cap cooperating with a joint socket of a first adjacent joint element, and of which a second part has a joint socket cooperating with a spherical cap of a second adjacent joint element, in which case at least one percutaneously arranged pin is clamped directly between the two parts by applying a tensile force to the central tensile force element.

4. The device as claimed in claim 1, further comprising at least one deflection element, which limits the maximum bending angle of the tensile force element, and is arranged in a longitudinal passage of an individual joint element, through which a longitudinal passage of the central tensile force element extends.

5. The device as claimed in claim 1, further comprising a stud arranged in a joint socket of a first joint element and limiting the pivotability of a ball joint formed by the joint socket and by a spherical cap of an adjacent, second joint element, and does this by protruding into an upper opening, located on the spherical cap, of the longitudinal passage of the second joint element.

6. The device as claimed in claim 1, wherein the joint elements are made of metal, a fiber-reinforced polymer material or a suitable plastic.

7. The device as claimed in claim 1, wherein the central tensile force element is a bundle, in particular at least one of a wire bundle, a carbon fiber bundle, and a bundle of another suitable plastic material or of a combination of the aforementioned materials.

8. The device as claimed in claim 1, further comprising a spring element which is connected to the central tensile force element and by means of which a tensile force is applicable to the central tensile force element.

9. The device as claimed in claim 1, further comprising a tensioning device by means of which a tensile force acting on the central tensile force element is generated.

10. The device as claimed in claim 9, wherein the tensioning device is arranged on one end of the support of the device.

11. The device as claimed in claim 9, wherein the tensioning device may be dismantled.

12. A method for the external fixation of fractured bones of a patient, particularly of the extremities, comprising:
providing a device as claimed in claim 1;
anchoring a plurality of percutaneously arranged pins with their proximal end in the bone tissue of the patient,
placing the distal ends of the plurality of percutaneously arranged pins on the support,
repositioning the bone fragments in their substantially anatomical original position, and
applying a tensile force to a central tensile force element of the device, such that the support of the device stiffens and at the same time the percutaneously arranged pins are fixed on the support by clamping and/or frictional engagement.

13. The method as claimed in claim 12, further comprising:
releasing the tensile force acting on the tensile force element, such that the reduction of the bone fragments is corrected, and applying a tensile force again to the tensile force element of the device, such that the support of the device is again stiffened and at the same time the percutaneously arranged pins are fixed on the support by clamping and/or frictional engagement.

14. A device for the external fixation of bone fragments of a patient, particularly of the extremities, with a support, which can be arranged outside the body of the patient comprises:
a plurality of stringed together joint elements forming the support; and
at least two percutaneously arranged pins which are adapted to be anchored with their proximal end in the bone tissue of the patient, securable by their distal end and fixable in their spatial position relative to each other;
which joint elements are stringed together on a central tensile force element, and two adjacent joint elements in each case together form a ball joint with a spherical cap and a joint socket, and the individual ball joints, and therefore the support, are reversibly fixable with a force fit, by frictional engagement, by applying a tensile force to the central tensile force element; and
which joint elements are configured such that by applying the tensile force to the central tensile force element at least one percutaneously arranged pin is clamped directly between the joint elements, while at the same time the individual ball joints, and therefore the support, are being reversibly fixed, wherein the joint socket suitable for forming a ball joint with a spherical cap includes at least one receiving groove for receiving a percutaneously arranged pin,
the at least one receiving groove being arranged radially adjacent to the joint socket such that when a ball joint is formed between the joint socket and the spherical cap the percutaneously arranged pin can be clamped between the spherical cap of the second joint element.

15. The device as claimed in claim 14, further comprising a spherical cap lying opposite the joint socket.

16. The device as claimed in claim 14, further comprising a second joint socket lying opposite the joint socket.

17. The device as claimed in claim 14, further comprising a longitudinal passage which extends between the spherical cap and the joint socket, with an upper opening of the longitudinal passage on the spherical cap, and with a lower opening of the longitudinal passage on the joint socket.

18. The device as claimed in claim 14, further comprising a deflection element which is arranged in the longitudinal passage and with which the maximum bending radius of a tensile force element extending through the longitudinal passage can be limited.

19. The device as claimed in claim 14, wherein a stud is arranged in the joint socket.

20. The device as claimed in claim 14, made of a fiber-reinforced polymer material or another suitable plastic or metal.

21. A device for the external fixation of bone fragments of a patient, particularly of the extremities, with a support, which can be arranged outside the body of the patient comprises:
a plurality of stringed together joint elements forming the support; and
at least two percutaneously arranged pins which are adapted to be anchored with their proximal end in the bone tissue of the patient, securable by their distal end and fixable in their spatial position relative to each other;
which joint elements are stringed together on a central tensile force element, and two adjacent joint elements in each case together form a ball joint with a spherical cap and a joint socket, and the individual ball joints, and therefore the support, are reversibly fixable with a force fit, by frictional engagement, by applying a tensile force to the central tensile force element; and
which joint elements are configured such that by applying the tensile force to the central tensile force element at least one percutaneously arranged pin is clamped directly between the joint elements, while at the same time the individual ball joints, and therefore the support, are being reversibly fixed, wherein the spherical cap and the joint socket are two pivotably arranged parts between which at least one receiving groove for receiving a percutaneously arranged pin is formed and in which groove the percutaneously arranged pin can be secured with a form fit and force fit by pressing the two parts together.

22. A device for the external fixation of bone fragments of a patient, particularly of the extremities, with a support, which can be arranged outside the body of the patient comprises:

a plurality of stringed together joint elements forming the support; and at least two percutaneously arranged pins which are adapted to be anchored with their proximal end in the bone tissue of the patient, securable by their distal end and fixable in their spatial position relative to each other;

which joint elements are stringed together on a central tensile force element, and two adjacent joint elements in each case together form a ball joint with a spherical cap and a joint socket, and the individual ball joints, and therefore the support, are reversibly fixable with a force fit, by frictional engagement, by applying a tensile force to the central tensile force element; and which joint elements are configured such that by applying the tensile force to the central tensile force element at least one percutaneously arranged pin is clamped directly between the joint elements, while at the same time the individual ball joints, and therefore the support, are being reversibly fixed, wherein the spherical cap suitable for forming a ball joint with the joint socket includes at least one receiving groove for receiving a percutaneously arranged pin, the at least one receiving groove being arranged on the spherical cap such that when a ball joint is formed between the spherical cap and the joint socket the pin can be clamped between the receiving groove and the joint socket.

23. The device as claimed in claim 3, comprising at least one receiving groove for receiving a percutaneously arranged pin, which receiving groove is formed between the two pivotably connected parts, such that the percutaneously arranged pin can be clamped between the two pivotably connected parts by applying a tensile force to the central tensile force element.

* * * * *

UNITED STATES PATENT AND TRADEMARK OFFICE
CERTIFICATE OF CORRECTION

PATENT NO.       : 8,685,022 B2  
APPLICATION NO.  : 12/999422  
DATED            : April 1, 2014  
INVENTOR(S)      : Lorenz et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 382 days.

Signed and Sealed this

Twenty-ninth Day of September, 2015

Michelle K. Lee
*Director of the United States Patent and Trademark Office*